US009310293B2

(12) United States Patent
Hanyu et al.

(10) Patent No.: US 9,310,293 B2
(45) Date of Patent: Apr. 12, 2016

(54) METHOD AND APPARATUS FOR EVALUATING ULTRAVIOLET RADIATION PROTECTION EFFECT, AND RECORDING MEDIUM

(71) Applicant: SHISEIDO COMPANY, LTD., Tokyo (JP)

(72) Inventors: Naoto Hanyu, Kanagawa (JP); Eiichi Negishi, Kyoto (JP); Kazuhiko Mibayashi, Kyoto (JP); Takafumi Sumiyama, Kyoto (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 14/647,148

(22) PCT Filed: Dec. 6, 2013

(86) PCT No.: PCT/JP2013/082866
§ 371 (c)(1),
(2) Date: May 26, 2015

(87) PCT Pub. No.: WO2014/092024
PCT Pub. Date: Jun. 19, 2014

(65) Prior Publication Data
US 2015/0308945 A1      Oct. 29, 2015

(30) Foreign Application Priority Data

Dec. 11, 2012   (JP) .................... 2012-270006

(51) Int. Cl.
*G01J 1/42* (2006.01)
*G01N 21/33* (2006.01)
*G01N 21/59* (2006.01)

(52) U.S. Cl.
CPC ............... *G01N 21/33* (2013.01); *G01N 21/59* (2013.01)

(58) Field of Classification Search
CPC ...... G01N 17/004; G01N 21/33; G01N 21/59
See application file for complete search history.

(56) References Cited

U.S. PATENT DOCUMENTS 7,014,842 B2      3/2006    Dueva-Koganov et al.
8,598,535 B2 *    12/2013   Miura .................... G01N 21/33
                                                                 250/372

(Continued)

FOREIGN PATENT DOCUMENTS

JP    2007-533957    11/2007
JP    2012-047489    3/2012

(Continued)

OTHER PUBLICATIONS

Korean Office Action dated Oct. 6, 2015.

(Continued)

*Primary Examiner* — Kiho Kim
(74) *Attorney, Agent, or Firm* — IPUSA, PLLC

(57) ABSTRACT

An evaluation method for evaluating an ultraviolet radiation protection effect in a measurement sample applied on an application member includes the first step of switching to a first filter for measuring a spectral transmittance before photodeterioration by emission of light from a light source, and measuring the spectral transmittance, the second step of switching to a second filter for ultraviolet irradiation and causing the photodeterioration by the emission of the light after the measurement by the first step, and thereafter, switching to the first filter and measuring the spectral transmittance, and the third step of evaluating the ultraviolet radiation protection effect based on a change over time in the spectral transmittance obtained by the second step. Each of the first and second filters includes multiple light source filters. The first filter includes ND filters switchable in accordance with the light amount of the light source in the light source filters.

8 Claims, 13 Drawing Sheets

(56) References Cited

U.S. PATENT DOCUMENTS

| | | |
|---|---|---|
| 2005/0013781 A1 | 1/2005 | Dueva-Koganov et al. |
| 2006/0228806 A1 | 10/2006 | Sens et al. |
| 2012/0050526 A1 | 3/2012 | Nagai et al. |
| 2012/0137958 A1 | 6/2012 | Mills et al. |

FOREIGN PATENT DOCUMENTS

| | | |
|---|---|---|
| JP | 2012-063323 | 3/2012 |
| JP | 2012-242215 | 12/2012 |
| WO | 2004/110366 | 12/2004 |

OTHER PUBLICATIONS

Japanese Office Action mailed Jan. 28, 2014.

International Search Report mailed on Jan. 28, 2014.

"UV-1000S Ultraviolet Transmittance Analyzer for Sunscreens", Internet Archive [online], Mar. 2, 2004 [retrieval date Jan. 14, 2014], Internet <URL:https://web.archive.org/web/20040302142454/http://labsphere.com/products/products.asp?CID=44&PID=384>.

ISO/FDIS 24443:2011(E) "Cosmetics-Sun protection test method-Determination of sunscreen UVA photoprotection in vitro", ISO/TC 217/SC /WG 7, Apr. 28, 2011.

* cited by examiner

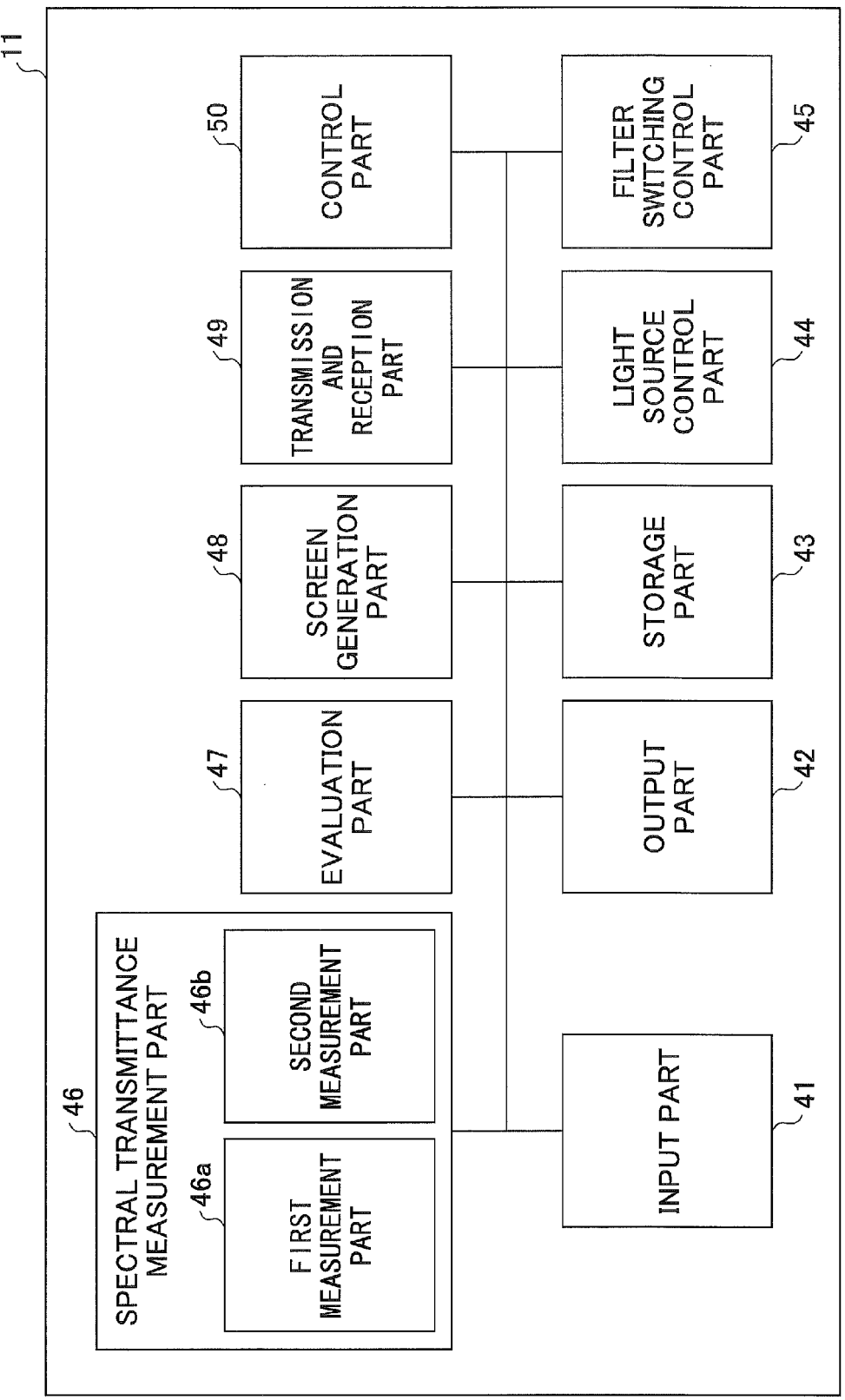

FIG.5

| No. | MEASUREMENT OBJECT | USE | RELATED MATTERS |
|---|---|---|---|
| 1 | | IRRADIATION | ADAPTED TO %RCEE |
| 2 | SPF MEASUREMENT | SPECTRAL TRANSMITTANCE MEASUREMENT (AT TIME OF AMOUNT OF LIGHT CORRESPONDING TO 1 MED/min) | OPTIMIZE DYNAMIC RANGE OF SPECTRAL TRANSMITTANCE MEASUREMENT BY SWITCHING ND FILTERS ACCORDING TO AMOUNT OF LIGHT OF LIGHT SOURCE |
| 3 | | SPECTRAL TRANSMITTANCE MEASUREMENT (AT TIME OF AMOUNT OF LIGHT CORRESPONDING TO 2 MED/min) | |
| 4 | | SPECTRAL TRANSMITTANCE MEASUREMENT (AT TIME OF AMOUNT OF LIGHT CORRESPONDING TO 3 MED/min) | |
| 5 | | SPECTRAL TRANSMITTANCE MEASUREMENT (AT TIME OF AMOUNT OF LIGHT CORRESPONDING TO 4 MED/min) | |
| 6 | UVA-PF MEASUREMENT | IRRADIATION | ISO/DIS24443-COMPLIANT |
| 7 | | SPECTRAL TRANSMITTANCE MEASUREMENT | LESS THAN 0.2 J/cm² PER MEASUREMENT |
| ... | ... | ... | ... |

FIG.8

| | BG18 | ND2% | ND3% | ND5.2% | ND10% |
|---|---|---|---|---|---|
| SPECTROPHOTOMETER | 38.4 | 47.0 | 30.9 | 37.7 | 10.3 |
| CONVENTIONAL APPARATUS | 40.9 | 40.5 | 29.3 | 35.9 | 9.9 |
| EMBODIMENT | 35.6 | 45.4 | 31.9 | 35.7 | 10.1 |

METHOD AND APPARATUS FOR EVALUATING ULTRAVIOLET RADIATION PROTECTION EFFECT, AND RECORDING MEDIUM

TECHNICAL FIELD

The present invention relates to methods and apparatuses for evaluating an ultraviolet radiation protection effect, and recording media.

BACKGROUND ART

The SPF (Sun Protection Factor) measured on human skin is recognized as a universal index that represents the effects of cosmetics for ultraviolet radiation prevention that prevent sunburn. Furthermore, an evaluation method for achieving highly accurate evaluation of an ultraviolet radiation protection effect in an actual usage environment or under actual usage conditions has been known (see, for example, Patent Document 1).

According to the technique illustrated in Patent Document 1, a change over time in a spectral transmission spectrum of a measurement sample in a predetermined wavelength range is measured at predetermined wavelength intervals, the correlation between light exposure time and an erythema effect size per predetermined time obtained by dividing the erythema effect size of the measurement sample by an erythema effect size per 1 MED is determined based on the measured change over time in the spectral transmission spectrum, and the in vitro predicted SPF of the measurement sample is calculated based on the time that a cumulative erythema effect size obtained from the determined correlation through time integration takes before reaching 1 MED.

PRIOR ART DOCUMENT

Patent Document

[Patent Document 1] Japanese Laid-Open Patent Application No. 2012-63323

SUMMARY OF THE INVENTION

Problems to be Solved by the Invention

According to the above-described conventional technique, however, in the case of using an integrating sphere to collect light transmitted through part of an application member on which a sample is applied (sample application part), a photomultiplier tube having high sensitivity or the like has to be used as a detector because of the poor efficiency of light collection of the integrating sphere. Furthermore, according to the conventional technique, it is necessary to obtain a spectrum result by mechanically performing a sequential scan using a monochromator or the like for light dispersion.

Furthermore, according to the conventional technique, the amplification factor of the photomultiplier tube is sequentially changed in order to expand the dynamic range. Furthermore, a predetermined stability period is necessary after the change. Therefore, according to the conventional technique, for example, a long time of approximately 2 minutes may be required to obtain a single spectrum.

Furthermore, in apparatuses for evaluating an ultraviolet radiation protection effect, it is desirable that the spectral radiant intensity of a light source for measuring spectral transmittance be less dependent on wavelengths. On the other hand, the spectral radiant intensity of a light source for ultraviolet irradiation is highly wavelength-dependent because of the necessity for having properties as pseudo sunlight, and is extremely low on the short wavelength side in a measurement range.

Here, for example, according to such a technique as illustrated in Patent Document 1 described above, the spectral radiant intensity is common to the light source for ultraviolet irradiation to the sample application part and the light source for measuring spectral transmittance. Therefore, the spectral transmittance of a dark sample having low transmittance may be measured with less accuracy on the short wavelength side in a measurement range where the spectral radiant intensity is extremely low.

According to an aspect, the present invention has an object of evaluating an ultraviolet radiation protection effect in a short time with high accuracy.

Means for Solving the Problems

According to an aspect of the present invention, a method for evaluating an ultraviolet radiation protection effect of a measurement sample applied on an application member includes a first step of selecting a first filter for measuring a spectral transmittance of the measurement sample before photodeterioration in a predetermined wavelength range by emission of light including ultraviolet radiation from a light source according to a preset light emission condition, and measuring the spectral transmittance, a second step of switching the first filter to a second filter for ultraviolet irradiation and causing the photodeterioration of the measurement sample through exposure to the ultraviolet radiation for a predetermined time after the measurement by the first step, and thereafter, switching the second filter to the first filter and measuring the spectral transmittance, and a third step of evaluating the ultraviolet radiation protection effect based on a change over time in the spectral transmittance obtained by repeating the second step over a predetermined time or a predetermined number of times.

According to an aspect of the present invention, an apparatus for evaluating an ultraviolet radiation protection effect of a measurement sample applied on an application member includes a light source control part configured to control a light source so as to emit light including ultraviolet radiation according to a preset light emission condition, a filter switching part configured to switch a plurality of filters for adjusting a wavelength range of the light source, and a spectral transmittance measurement part configured to measure a spectral transmittance of the application member on which the measurement sample is applied with respect to the light emitted from the light source, using the light source control part and the filter switching control part.

According to an aspect of the present invention, an evaluation program for causing a computer to operate as the apparatus for evaluation as set forth above is recorded on a computer-readable recording medium.

Effects of the Invention

According to an aspect of the present invention, it is possible to evaluate an ultraviolet radiation protection effect in a short time with high accuracy.

BRIEF DESCRIPTION OF THE DRAWINGS

Other objects, features and advantages of the present invention will become more apparent from the following detailed description when read in conjunction with the accompanying drawings, in which:

FIG. 2 is a diagram illustrating a functional configuration of an evaluation apparatus according to an embodiment of the present invention.

FIG. 5 is a diagram illustrating filter configurations of a filter part according to an embodiment of the present invention.

FIG. 8 is a diagram illustrating SPF results according to an embodiment of the present invention.

EMBODIMENTS FOR CARRYING OUT THE INVENTION

An embodiment of the present invention includes timely switching the spectral radiant intensity with respect to a light source between a spectral radiant intensity for exposing part of an application member on which a measurement sample is applied (sample application part) to ultraviolet radiation and a spectral radiant intensity for measuring the spectral transmittance of the sample application part (including the applied measurement sample) by, for example, switching multiple optical filters.

Furthermore, an embodiment of the present invention uses a spectrometer (evaluation system) that employs, for example, a linear image sensor. As a result, it is possible to obtain the spectral intensity of light transmitted through the sample application part with respect to the entirety of a specified wavelength range at a time in a short time (selectable within the range of, for example, 0.01 seconds to 10 seconds). Accordingly, it is possible to reduce time in which a filter for measuring spectral transmittance used in an evaluation process is selected.

A detailed description is given below, with reference to the accompanying drawings, of embodiments in which a method and apparatus for evaluating an ultraviolet radiation protection effect and a recording medium in which an evaluation program is recorded, which have the above-noted features, are suitably implemented.

Figure 1A:
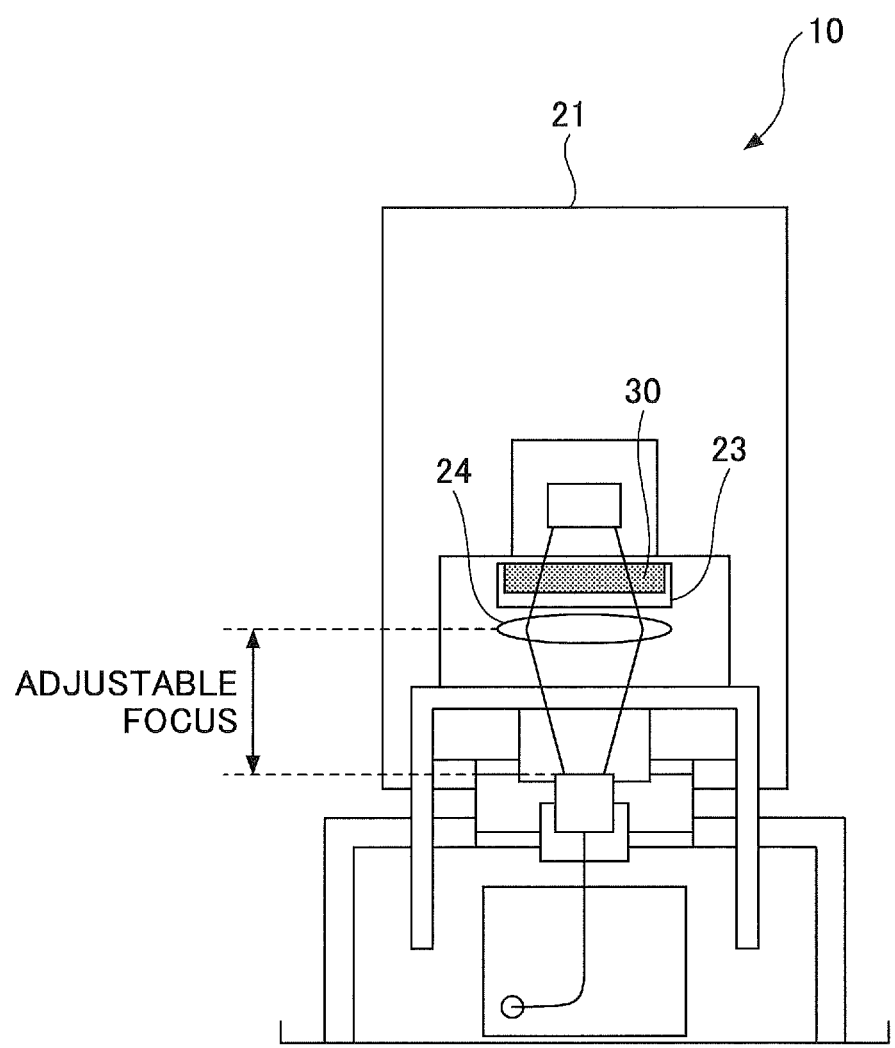
FIG. 1A is a front view of an evaluation system according to an embodiment of the present invention.
Figure 1B:
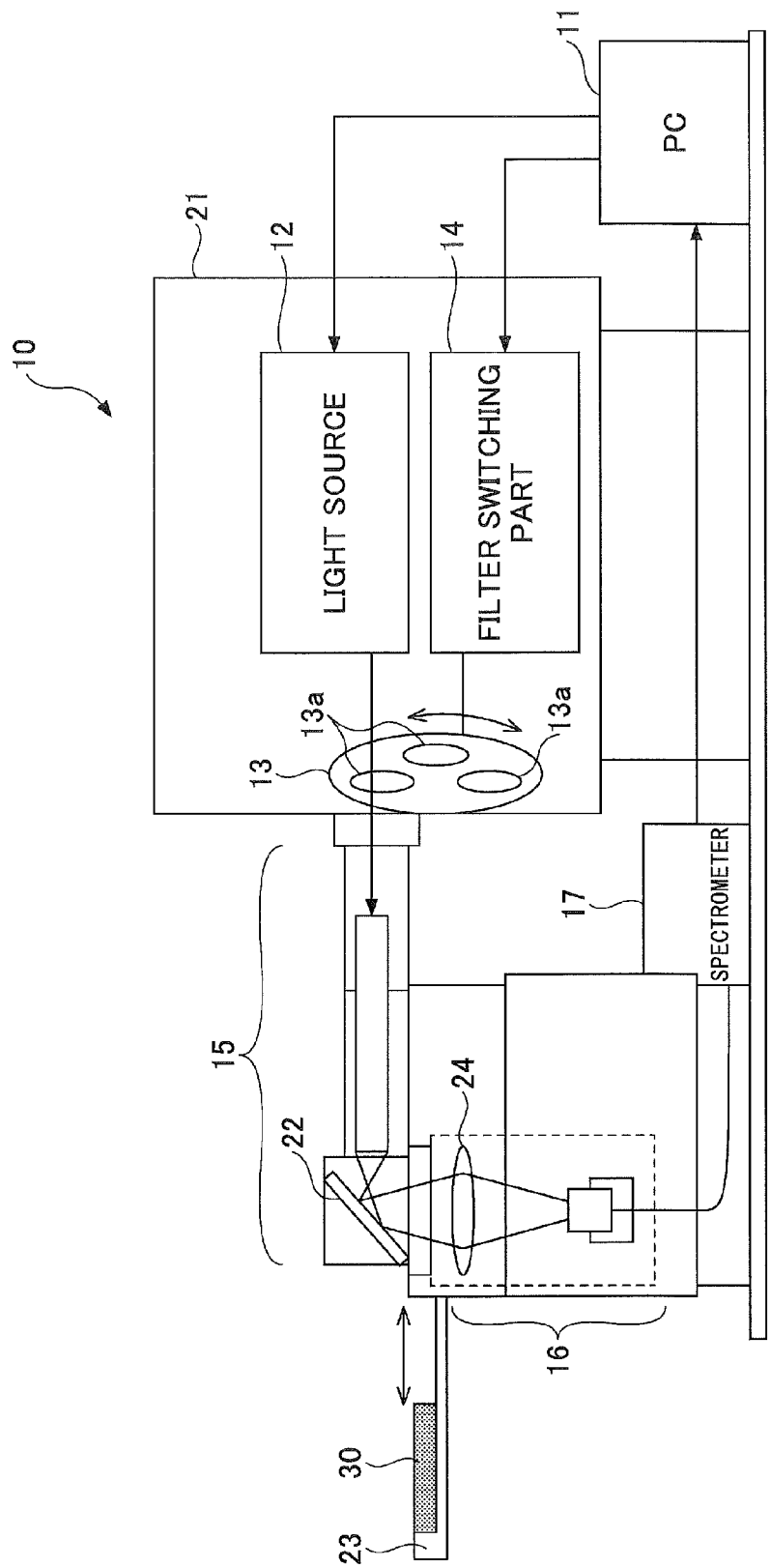
FIG. 1B is a side view of the evaluation system illustrated in FIG. 1A.

First, a description is given of a system for evaluating an ultraviolet radiation protection effect according to an embodiment of the present invention. FIGS. 1A and 1B are diagrams illustrating an evaluation system according to an embodiment of the present invention. FIGS. 1A and 1B are a front view and a side view, respectively, of an evaluation system 10.

The evaluation system 10 illustrated in FIGS. 1A and 1B includes a personal computer (PC) 11 as an example of the evaluation apparatus, a light source 12, a filter part 13, a filter switching part 14 (a filter changer), a rod lens 15, a light pipe 16, and a spectrometer 17. According to the evaluation system 10 illustrated in FIGS. 1A and 1B, the light source 12, the filter part 13, and the filter switching part 14 may be provided in a housing 21 as a non-limiting configuration. Furthermore, the rod lens 15 includes a mirror 22. The evaluation system 10 includes a holder 23 that is movable with an application plate (application member) 30 on which a sample to be measured (measurement sample) is applied being placed on the holder 23. The light pipe 16 includes a condenser lens 24.

The PC 11 executes a preset process by controlling devices in the evaluation system 10, and obtains a corresponding measurement. Furthermore, the PC 11 evaluates an ultraviolet radiation protection effect based on results such as the obtained measurement. The PC 11 is not limited to a general-purpose PC, and may be one of various information processing apparatuses such as servers, notebook PCs, tablet terminals, and smartphones.

The light source 12 emits ultraviolet radiation and the like of predetermined wavelengths with predetermined timing based on a control signal from the PC 11 in order to, for example, evaluate an ultraviolet radiation protection effect.

The filter 13 includes one or more optical filters 13a. The filter part 13 places the optical filter 13a selected by the filter switching part 14 in the light path of the ultraviolet radiation emitted from the light source 12. The filter part 13 may include optical filters 13a that differ in the band of light to transmit. This makes it possible to switch the wavelengths of light that passes through the optical filter of the filter part 13 to the wavelengths of a predetermined band.

The filter switching part 14 is capable of switching the one or more optical filters 13a provided in the filter part 13 based on a predetermined condition based on a control signal from the PC 11. In the case of FIGS. 1A and 1B, the filters are switched by placing a predetermined filter on an optical axis by rotating a circular plate in which the different optical filters 13a are provided about the center of the plate. The configuration of switching filters is not limited to this. For example, a predetermined optical filter may be positioned on an optical axis by providing multiple optical filters in a slidable plate and sliding the plate in a predetermined direction.

The rod lens 15 enlarges or reduces an exposure area in a plane by moving a lens relative to the light path of ultraviolet radiation obtained through any of the optical filters 13a of the filter part 13. Specifically, light is made uniform and the area of a light path is enlarged inside the rod lens 15.

Furthermore, the rod lens 15 redirects the light path toward the light pipe 16 with the mirror 22. The mirror 22 does not have to be provided in the rod lens 15 if there is no need to redirect the light path.

The light pipe 16 lets light that has passed through the application plate 30 from the rod lens 15 side enter the condenser lens 24, collects entering ultraviolet light with the condenser lens 24 and the like, and outputs the collected ultraviolet light to the spectrometer 17. The light pipe 16, which is capable of adjusting focus, can perform adjustment so as to maximize the output of collected light, for example, but is not limited to this configuration. Furthermore, the condenser lens 24, which is, for example, 40 mm in diameter, is not limited to this configuration, and may be arbitrarily set as required.

The light pipe 16, for which, for example, a synthetic quartz light pipe (for example, of a hexagonal prism shape) or the like may be used, is not limited to this. Furthermore, the light pipe 16 may employ, for example, an optical fiber or the like to output collected light to the spectrometer 17. Accordingly, the light collected onto an end face of the light pipe 16 is made uniform while being reflected inside the light pipe 16, and part of the light is input to the spectrometer 17 via an input fiber of 0.6 mm in diameter of the spectrometer 17. This makes it possible to prevent degradation of light at a transmission time.

The spectrometer 17 detects light input from the light pipe 16, and outputs information obtained from the detected light (for example, the electromagnetic wave spectrum of light, physical quantities of light such as intensity, etc.) to the PC 11. Furthermore, the spectrometer 17 may, for example, employ a transmission holographic grating made of quartz, obtain input light as an image with a linear image sensor or the like, and output obtained image data to the PC 11 as measurement results. For example, the spectrometer 17 may output light information obtained with a CCD (Charge Coupled Device) UV (ultraviolet) spectrometer or the like to the PC 11. Furthermore, the spectrometer 17 is also capable of performing high dynamic range (HDR) processing.

That is, according to this embodiment, by using, as the spectrometer 17, a spectrometer that includes no mechanically movable part and uses a semiconductor linear image sensor without a movable part in which light dispersion and detection are integrated as described above, it is possible to obtain the spectral intensity of light transmitted through the sample application part with respect to the entirety of a specified wavelength range at a time in a short time. As a result, it is possible to, for example, reduce time in which a filter for measuring spectral transmittance is selected.

Furthermore, according to this embodiment, it is possible to improve the efficiency of light collection by using a lens and a synthetic quartz light pipe or the like as described above. In the case of a linear image sensor, it is possible to expand a final dynamic range by varying exposure (accumulation) time (selectable within the range of, for example, 0.01 seconds to 10 seconds) and combining successively obtained results in the PC 11.

Furthermore, according to this embodiment, by including the filter switching part 14 that switches the optical filters 13a, it is possible to support another method of evaluating an ultraviolet radiation protection effect that addresses photodeterioration by suitably selecting each filter 13a. Specifically, it is possible to support, for example, a photodeterioration UVA-PF measurement or the like, which is not the only supportable method of evaluating an ultraviolet radiation protection effect that addresses photodeterioration.

Furthermore, according to this embodiment, the holder 23 of the above-described evaluation system 10 illustrated in FIGS. 1A and 1B may include a Peltier device or the like. By heating the holder 23 with the heat generated from the Peltier device by application of electric current, it is possible to control the temperatures of the application plate 30 and a sample attached to the holder 23. Accordingly, for example, it is possible to adjust the temperature of a sample to approximately 25° C. to 35° C. at the time of exposure as defined by the ISO24443 protocol.

Furthermore, as described above, the intensity of the light source 12 according to this embodiment may be approximately 0.001 MED/min to approximately 20.0 MED/min, and the amount of application of a sample may be approximately 0.01 mg/cm$^2$ to approximately 10.0 mg/cm$^2$. The intensity of the light source 12 and the amount of application of a sample, however, are not limited to these ranges. Furthermore, the arithmetic mean roughness (Sa value) of the application plate 30 may be, but is not limited to, approximately 0.01 μm to approximately 400 μm. As the application plate 30, a plate on which, for example, a cosmetic product for ultraviolet radiation prevention is applied as a measurement sample may be used, or a glass filter may be used to improve the reproducibility of measurement.

Next, a description is given of a functional configuration of the above-described PC (evaluation apparatus) 11. FIG. 2 is a diagram illustrating a functional configuration of a PC according to an embodiment of the present invention. The PC 11 illustrated in FIG. 2, which serves as an example of the evaluation apparatus, includes an input part 41, an output part 42, a storage part 43, a light source control part 44, a filter switching control part 45, a spectral transmittance measurement part 46, an evaluation part 47, a screen generation part 48, a transmission and reception part 49, and a control part 50.

The input part 41 receives various inputs such as inputs of the starts and ends of various instructions and inputs of settings from a user who uses the PC 11. Specifically, the input part 41 receives instructions such as an instruction to control a light source, an instruction to control filter switching, an instruction to measure spectral transmittance, an instruction to perform evaluation, an instruction to generate a screen, and an instruction to perform transmission or reception according to this embodiment.

Information obtained by the input part 41 may be input through an input interface such as a keyboard or a mouse, input through a touchscreen panel using a screen, or input using operation keys or the like. Furthermore, the input part 41 may include a voice input part that inputs voice through, for example, a microphone or the like.

The output part 42 outputs the contents of an input by the input part 41, the contents of a process executed based on the contents of the input, etc. For example, the output part 42 may include a display part such as a display or a monitor in the case of performing outputting by displaying a screen, and may include a voice output part such as a loudspeaker in the case of performing outputting by voice. Furthermore, the input part 41 and the output part 42 may be a single input/output part such as a touchscreen panel.

The storage part 43 stores various kinds of information required according to this embodiment. Specifically, the storage part 43 stores various settings information and the progress and results of execution of various processes at a measurement time. Furthermore, the storage part 43 is capable of reading the stored various kinds of information and writing various kinds of information with predetermined timing as required. The storage part 43 includes, for example, a hard disk and a memory.

The light source control part 44 controls the emission timing, intensity, etc., of the light source 12, and outputs its control signal to the light source 12 to cause the light source 12 to emit ultraviolet radiation and the like of predetermined wavelengths, in the case of measuring spectral transmittance.

The filter switching control part 45 selects a predetermined filter from among the one or more filters 13a provided in the filter part 13, which are switched by the filter switching part 14, and controls the timing of switching to the predetermined filter, in the case of measuring spectral transmittance. The filter switching control part 45 generates a filter switching control signal and outputs the generated signal to the filter switching part 14, so that the switching to the predetermined filter is performed.

The spectral transmittance measurement part 46, for example, measures spectral transmittance for evaluating an ultraviolet radiation protection effect using the above-described evaluation system 10 illustrated in FIGS. 1A and 1B. Specifically, the spectral transmittance measurement part 46 obtains measurement results of spectral transmittance based on predetermined conditions by performing light source control with the light source control part 41 and filter switching control with the filter switching control part 45.

Specifically the spectral transmittance measurement part 46 includes, for example, a first measurement part 46a and a second measurement part 46b. The first measurement part 46a refers to, for example, first selecting a filter for measuring spectral transmittance and measuring spectral transmittance before photodeterioration of a measurement sample. The second measurement part 46b refers to, for example, switching the filter for measuring spectral transmittance to a filter for ultraviolet irradiation and causing photodeterioration of the applied measurement sample for a predetermined time after performing the above-described measurement with the first measurement part 46a, and thereafter, switching the filter for ultraviolet irradiation to the filter for measuring spectral transmittance again and measuring spectral transmittance after the photodeterioration due to exposure to ultraviolet radiation for the predetermined time. The processing of the first and second measurement parts 46a and 46b is not limited to the processing described above.

The evaluation part 47, for example, evaluates a protection effect against ultraviolet radiation emitted under real-life usage conditions or in a real-life usage environment with high accuracy based on the above-described measurement results obtained by the spectral transmittance measurement part 46.

Specifically, the evaluation part 47, for example, continuously obtains measurement results of time-varying spectral transmittance for a predetermined time, considering the above-described photodeterioration and spectral transmittance measurement in the second measurement part 46b as one cycle, and records the changes over time in spectral transmittance in the storage part 43 or the like. Furthermore, when the changes over time in spectral transmittance are measured for the predetermined time, the evaluation part 47 performs evaluation of an ultraviolet radiation protection effect that takes photodeterioration into consideration based on the changes over time in spectral transmittance.

The screen generation part 48 generates a setting screen or the like that displays the results obtained by the above-described configurations and on which various settings are input, and causes the output part 42 to output the generated screen. A description is given below of a screen generated by the screen generation part 48.

The transmission and reception part 49 is, for example, a communication part for transmitting data to and receiving data from external apparatuses such as the light source 12, the filter switching part 14, and the spectrometer 17 and other external apparatuses via a communication network connected to the Internet, a LAN (Local Area Network), and other various kinds of cables. The transmission and reception part 49 is capable of receiving various kinds of information that have been stored in external apparatuses and the like and is also capable of transmitting the processing results of the PC 11 to external apparatuses and the like via the communication network or the like.

The control part 50 performs overall control of the constituent parts of the PC 11. Specifically, the control part 50, for example, performs individual control operations related to evaluation of an ultraviolet radiation protection effect based on instructions or the like from a user or the like. Here, the individual control operations include, but are not limited to, for example, the control of the light source 12 by the light source control part 44, the filter switching control by the filter switching control part 45, the measurement of spectral transmittance by the spectral transmittance measurement part 46, the evaluation of an ultraviolet radiation protection effect by the evaluation part 47, and the screen control by the screen generation part 48 as described above. These control operations may be performed based on execution of a program or execution of a predetermined event, command or the like at the instruction of a user or the like. The modes of implementing these control operations, however, are not limited to these.

Here, according to the above-described evaluation apparatus, it is possible to implement the evaluation process according to this embodiment by creating an execution program (evaluation program) capable of causing a computer to execute the functions and installing the execution program in, for example, a general-purpose PC or a server. Here, a description is given of a hardware configuration of a computer capable of implementing the evaluation process according to an embodiment of the present invention.

Figure 3:
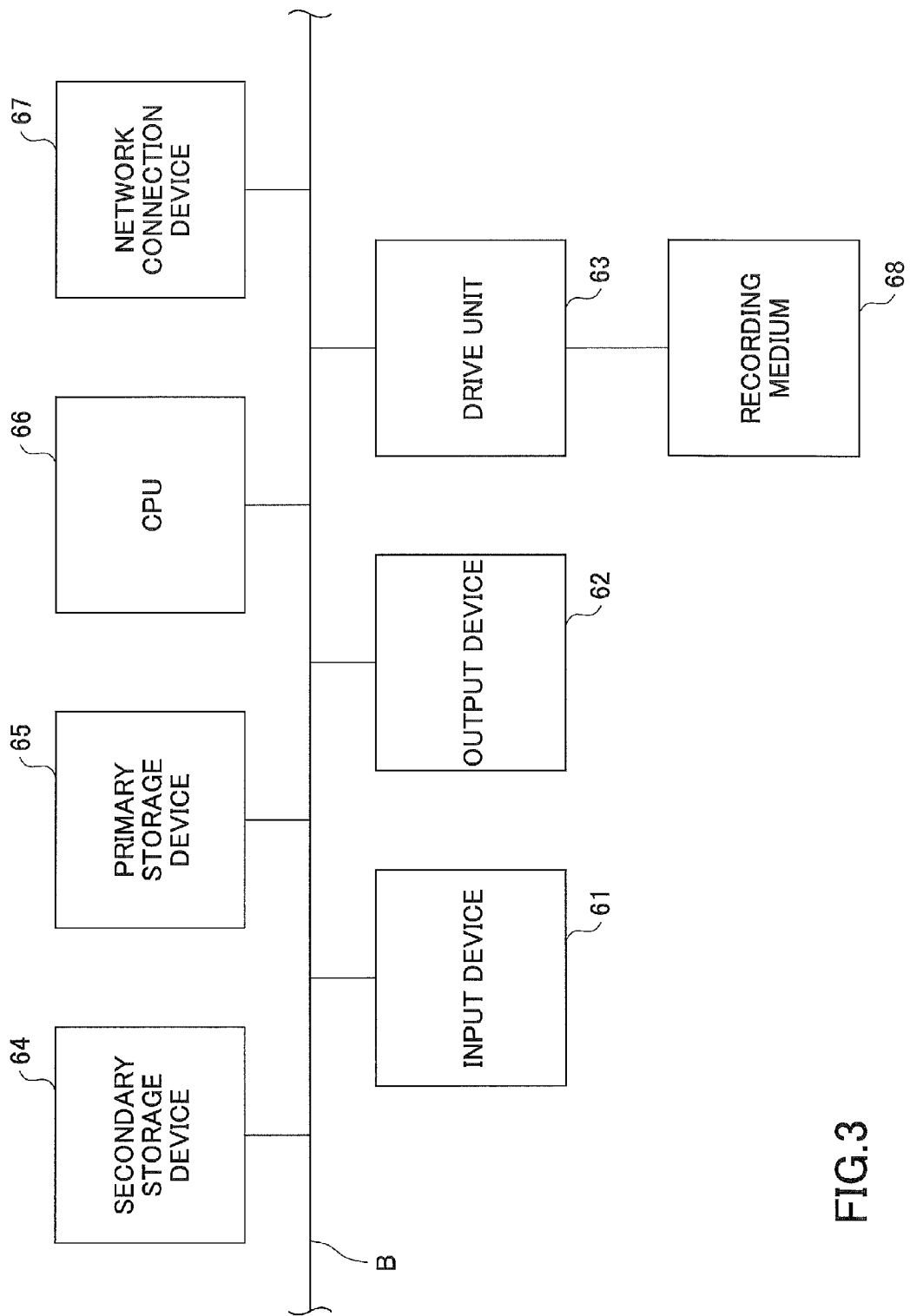
FIG. 3 is a diagram illustrating a hardware configuration capable of implementing an evaluation process according to an embodiment of the present invention.

FIG. 3 is a diagram illustrating a hardware configuration capable of implementing the evaluation process. Referring to FIG. 3, a computer body includes an input device 61, an output device 62, a drive unit 63, a secondary storage device 64, a primary storage device 65, a central processing unit (CPU) 66, and a network connection device 67, which are interconnected by a system bus B.

The input device 61 includes, for example, a keyboard and a pointing device such as a mouse, which are operated by a user or the like, and a voice input device such as a microphone. The input device 61 inputs an instruction to execute a program from a user or the like, various kinds of operation information, information for activating software, etc.

The output device 62 includes a display that displays various kinds of windows for operating the computer body and data, which are for performing processing according to this embodiment, and is capable of displaying the progress and results of execution of a program as a result of execution of a control program by the CPU 66. Furthermore, the output device 62 is capable of presenting a user or the like with the above-described processing results and the like by printing the processing results and the like on a printing medium such as paper.

Here, the execution program installed in the computer body according to this embodiment is provided by way of a portable recording medium 68 such as a universal serial bus (USB) memory, a CD-ROM, or a DVD, or the like. The recording medium 68 on which the execution program is recorded may be loaded into the drive unit 63. The execution program contained in the recording medium 68 is installed in the secondary storage device 64 from the recording medium 68 via the drive unit 63 based on a control signal from the CPU 66.

The secondary storage device 64 stores the execution program according to this embodiment, a control program provided in a computer, the progress and results of execution, etc., based on a control signal from the CPU 66. Furthermore, the secondary storage device 64 is capable of reading necessary information from the stored information and writing necessary information based on control signals or the like from the CPU 66.

The secondary storage device 64 includes, for example, a hard disk drive (HDD) or a solid state drive (SSD), and corresponds to, for example, the above-described storage part 43.

The primary storage device 65 stores the execution program read from the secondary storage device 64 by the CPU 66, etc. The primary storage device 65 includes a read only memory (ROM) and a random access memory (RAM).

The CPU 66 is capable of implementing processes by controlling processes of the entire computer, such as various kinds of operations and the inputting of data to and the outputting of data from hardware constituent parts, based on control programs such as an operating system and the execution program stored in the primary storage device 65. Various kinds of information necessary during execution of a program and the like may be obtained from and the results of execution may be stored in the secondary storage device 64.

Specifically, the CPU 66, for example, causes the evaluation program installed in the secondary storage device 64 to be executed based on an instruction to execute a program obtained from the input device 61, or the like, thereby executing a process corresponding to the evaluation program in the primary storage device 65.

For example, the CPU 66 performs control operations such as the control of the light source 12 by the light source control part 44, the filter switching control by the filter switching control part 45, the measurement of spectral transmittance by the spectral transmittance measurement part 46, and the evaluation of an ultraviolet radiation protection effect by the evaluation part 47 as described above by causing the evaluation program to be executed. The processes in the CPU 66 are not limited to those described above. The processes executed by the CPU 66 (the progress and results of execution), etc., may be stored in the secondary storage device 64 as required.

The network connection device 67 obtains the execution program, software, various kinds of commands, etc., from external apparatuses or the like connected to the communication network by connecting to the connection network or the like based on a control signal from the CPU 66. Furthermore, the network connection device 67 is capable of providing external apparatuses or the like with the results of execution obtained by executing a program or the execution program itself according to this embodiment.

With the hardware configuration as described above, it is possible to execute the evaluation process with respect to a database according to this embodiment. Furthermore, by installing a program, it is possible to easily implement the evaluation process according to this embodiment with a general-purpose PC or the like.

Figure 4:
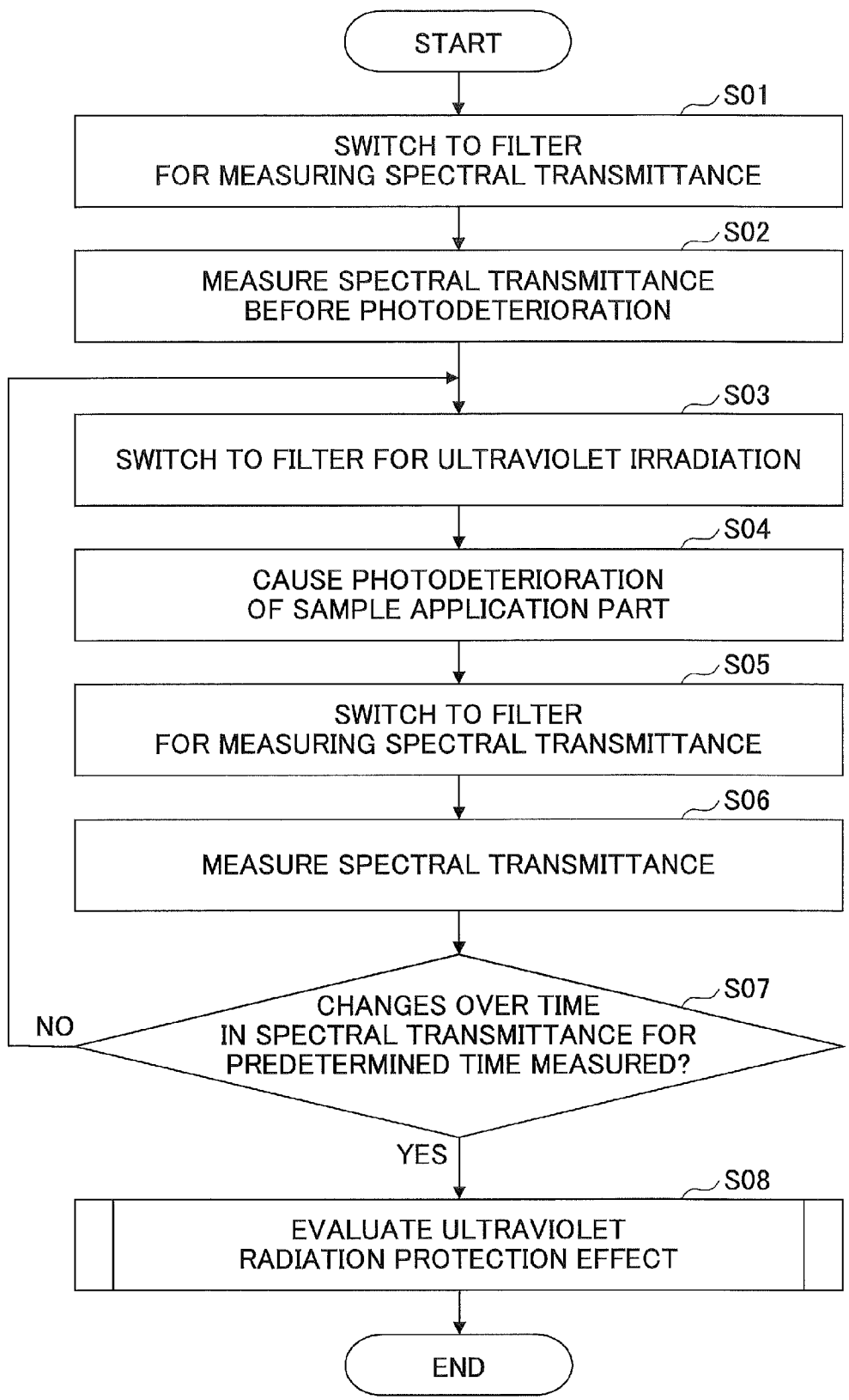
FIG. 4 is a flowchart illustrating an evaluation process according to an embodiment of the present invention.

Next, a description is given of an evaluation process according to an embodiment of the present invention. FIG. 4 is a flowchart illustrating an evaluation process according to an embodiment of the present invention. In the case illustrated in FIG. 4, a description is given of an evaluation process including a measurement process.

At step S01 of FIG. 4, a filter for measuring spectral transmittance is selected from among multiple preset filters by filter switching in the filter switching part 14 controlled by the filter switching control part 45, and at step S02, the spectral transmittance of a measurement sample before photodeterioration in a predetermined wavelength range is measured (for example, for approximately 10 seconds) by emission of light including ultraviolet radiation from a light source according to a preset light emission condition. The above-described process of steps S01 and S02 corresponds to a first step (the first measurement part 46*a*).

Thereafter, at step S03, the filter for measuring spectral transmittance is switched to a filter for ultraviolet irradiation, and at step S04, the photodeterioration of a sample application part is caused for a predetermined time. In the process of step S03, the filter used in the process of step S01 is switched to a different filter, and this switching of filters is performed by the filter switching part 14. Furthermore, the predetermined time at step S04 is preferably, but is not limited to, for example, approximately 2 minutes.

Next, at step S05, the filter for ultraviolet irradiation is switched to the filter for measuring spectral transmittance again, and at step S06, the spectral transmittance after the photodeterioration due to exposure to ultraviolet radiation for the predetermined time is measured (for example, for approximately 10 seconds). The above-described process of steps S03 through S06 corresponds to a second step (the second measurement part 46*b*).

Thereafter, considering the above-described photodeterioration and spectral transmittance measurement as one cycle, the measurement results of time-varying spectral transmittance for a predetermined time are successively obtained, and the changes over time in spectral transmittance are recorded in the storage part 43 or the like. That is, at step S07, it is determined whether changes over time in spectral transmittance for a predetermined time are measured, and if not measured (NO at step S07), the evaluation process returns to step S03. If changes over time in spectral transmittance for a predetermined time are measured (YES at step S07), at step S08, the evaluation of an ultraviolet radiation protection effect that takes photodeterioration into consideration based on the changes over time in spectral transmittance is performed. The above-described process of steps S07 and S08 corresponds to a third step (evaluation part).

In the process of step S08, the ultraviolet radiation protection effect is evaluated by, for example, calculating the "erythema effect size" from the amount of light transmitted through the measurement sample, and calculating an SPF by determining the end point of reaction from the "cumulative erythema effect size" obtained by accumulating the calculated values over the exposure time. Here, a specific description of the above-described technique, for which, for example, the evaluation technique as illustrated in Patent Document 1 may be used, is omitted.

Furthermore, according to the above-described process, the measurement results of time-varying spectral transmittance for a predetermined time are successively obtained, considering the photodeterioration and spectral transmittance measurement as one cycle. This, however, is non-limiting, and the measurement results of time-varying spectral transmittance for a predetermined number of times may be successively obtained, and the changes over time in spectral transmittance may be recorded in the storage part 43 or the like. In this case, in the process of step S07, it is determined whether changes over time in spectral transmittance for a predetermined number of times are measured.

Here, a specific description is given of the filter part 13. FIG. 5 is a diagram illustrating configurations of filters of a filter part according to an embodiment of the present invention. In the case of FIG. 5, items such as filter identification information (No.), a measurement object, use, and related matters are illustrated. The light source filters (optical filters 13*a*) provided in the filter part 13 according to this embodiment may be, but are not limited to, for example, light source filters for measuring spectral transmittance (for SPF measurement) and light source filters for irradiation (for ultraviolet radiation deterioration) (for UVA-PF measurement).

That is, the filter part 13 is prepared with multiple light source filters for each use. As a result, for example, in SPF measurement, it is possible to use a light source spectrum for measurement that is not cut on the short wavelength side and the long wavelength side relative to a light source spectrum for irradiation by switching filters, so that it is possible to measure transmittance with accuracy on the short wavelength side and the long wavelength side. In particular, the transmittance on the short wavelength side is significantly weighted in SPF calculations, and accordingly, greatly affects measured SPFs.

In the case of FIG. 5, the filter part 13 includes, as filters for SPF measurement, five kinds of filters for irradiation (adapted to % RCEE) and multiple spectral transmittance measurements (at the time of the amount of light corresponding to 1 MED/min, 2 MED/min, 3 MED/min, and 4 MED/min). The filters for SPF measurement of the filter part 13, however, are not limited to these.

The above-noted % RCEE indicates, for example, relative cumulative erythemal effectiveness. Furthermore, MED means minimal erythema dose. The MED on human skin is the minimum amount of ultraviolet radiation (no provision as to in which unit to display the amount of ultraviolet radiation) that first causes clearly-bounded slight erythema over an area of two-thirds or more of the exposed part in 6 to 24 hours after exposure to ultraviolet radiation. Based on this, the SPF may be calculated as (the minimal erythema dose in the case of protecting skin from ultraviolet radiation with a measurement sample)/(the minimal erythema dose in the case of exposing skin directly to ultraviolet radiation).

Furthermore, according to the filters for spectral transmittance measurements, it is possible to optimize the dynamic range of spectral transmittance measurement by switching ND filters (neutral density filters) in accordance with the amount of light of a light source. This is because the time required for one scan decreases as the dynamic range becomes narrower.

Furthermore, in the case of FIG. 5, the filter part 13 includes, as filters for UVA-PF measurement, filters supporting irradiation (ISO24443-compliant) and spectral transmittance measurement (less than 0.2 J/cm$^2$ per measurement). The filters for UVA-PF measurement, however, are not limited to these. Furthermore, the kinds of filters are not limited to the examples of FIG. 5.

The light source filter for irradiation may adjust the band of a light source by, for example, superposing multiple filters. Furthermore, the light source filter for measuring spectral transmittance may employ, for example, reflection ND filters. For example, the total of two filters, one of ND1% and one of ND5%, may be superposed to be used as a light source filter of ND0.05% (0.0005=0.01×0.05). The light source filter for measuring spectral transmittance, however, is not limited to this. ND is an initialism of Neutral Density, and "NDxx %" indicates, for example, a specification value of transmittance or the like.

Figure 6A:
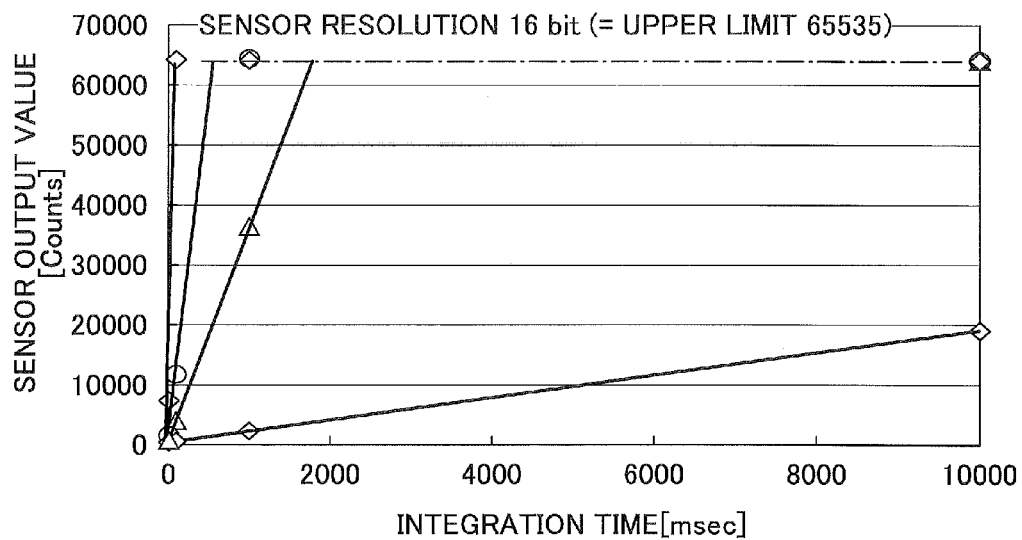
FIGS. 6A and 6B illustrate high dynamic range processing according to an embodiment of the present invention.
Figure 6B:
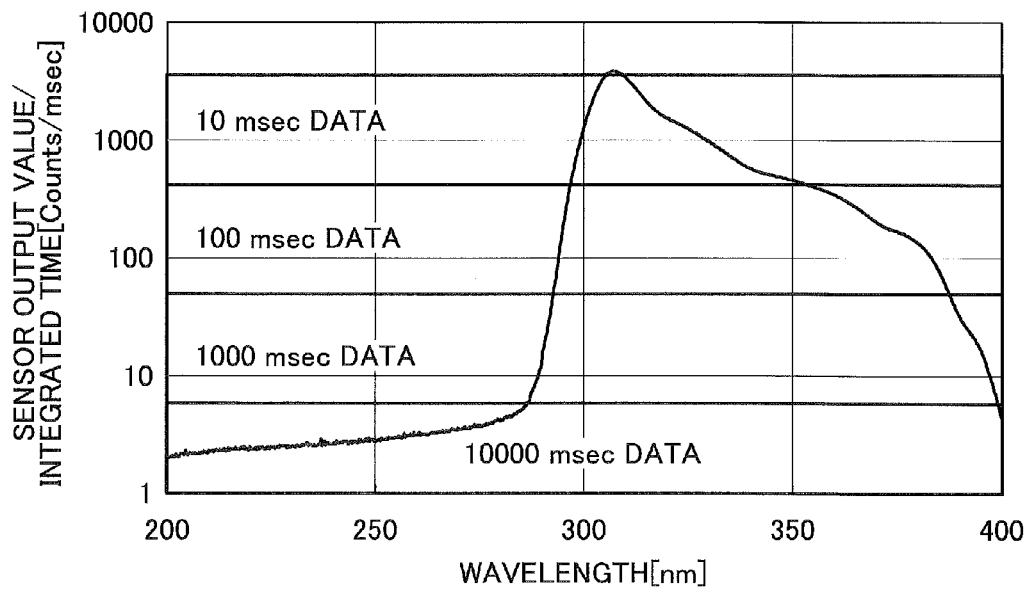

Here, a description is given of HDR processing in the spectrometer 17 according to an embodiment of the present invention. FIGS. 6A and 6B illustrate high dynamic range processing. FIG. 6A is a graph for illustrating the dependence of image sensor output on integration time, where the horizontal axis indicates integration time [msec] and the vertical axis indicates sensor output value [Counts]. Furthermore, FIG. 6B indicates an obtained spectrum, where the horizontal axis indicates wavelength [nm] and the vertical axis indicates sensor output value/integrated time [counts/msec].

The image sensor used at the time of the measurement illustrated in the case of FIG. 6A has a resolution of 16 bits, but is capable of varying the integration time from 10 msec to 10000 msec. Using this, a program to obtain a spectrum was created, and expanding the dynamic range while maintaining linearity was verified.

According to the integration time dependence of the sensor output illustrated in FIG. 6A, the linearity of the sensor output is maintained relative to the integration time in a region where the sensor is not saturated. Thus, according to this embodiment, as a data obtaining procedure, first, a group of spectra having different integration times is obtained, and in descending order of the length of the integration time, the data are switched to the spectral data of the following shorter integration time when the sensor output becomes close to a 16 bit upper limit (in practice, 63500). Next, according to this embodiment, it is possible to determine final spectral data by dividing the sensor output by the integration time and synthesizing the outputs.

As illustrated in FIG. 6A, the sensor output values [Counts] are values proportional to the incident intensity [mW/cm$^2$]. Accordingly, the linearity of the sensor output is maintained relative to the integration time in a region where the sensor is not saturated ($R^2$=approximately 0.99999).

In the case of FIG. 6B, the sensor's own noise (data without entry of light) was 1 to 1.7 in "(sensor output)/(integration time)." Furthermore, the dynamic range was nearly three digits (1.7 to 6553.5 in combined output). Furthermore, in the maximum range, it has been possible to obtain a spectrum of 200 nm to 400 nm within a little over 10 seconds. When the dynamic range may be approximately first two digits, it is possible to obtain a spectrum within 1 second.

Furthermore, it has been possible to achieve a higher scan speed, which is 1/10 to 1/100 of what it was (approximately 120 seconds). In FIG. 6B, the sensor output values [Counts] are values proportional to the incident intensity [mW/cm$^2$].

Figure 7:
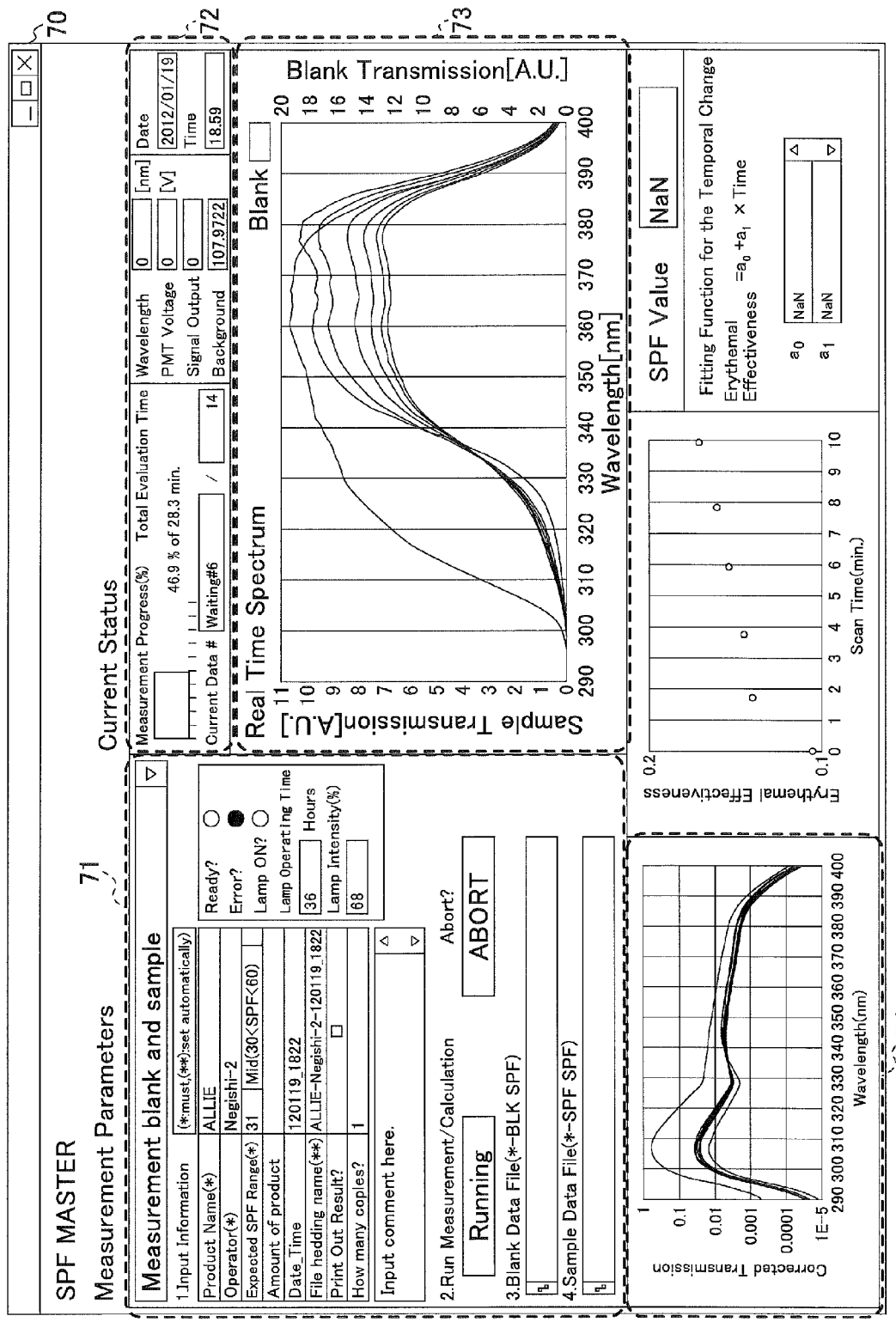
FIG. 7 is a diagram for illustrating a screen according to an embodiment of the present invention.

Next, a description is given of a screen generated by the screen generation part 48. FIG. 7 is a diagram for illustrating a screen according to an embodiment of the present invention. A screen 70 illustrated in FIG. 7 includes a measurement parameter setting region 71, a count status display region 72, a transmission spectrum result display region 73, and an SPF calculation result display region 74. According to this embodiment, the display contents and display layout of the screen are not limited to these.

According to this embodiment, a user sets various kinds of parameters with respect to settings information shown in the measurement parameter setting region 71 with the input part 41 or the like. Thereafter, a process is executed, so that a real-time count status with respect to a measurement is displayed in the count status display region 72, and the result is displayed in the transmission spectrum result display region 73.

Furthermore, according to this embodiment, because the sensitivity of skin differs from person to person, an SPF may be calculated from changes over time in area in consideration of its weighting (for example, the erythema factor or the like) and displayed in the SPF calculation result display region 74.

Next, a description is given of SPF results according to an embodiment of the present invention. FIG. 8 is a diagram illustrating SPF results according to this embodiment. In the case of FIG. 8, a spectrophotometer and, for example, a conventional apparatus as illustrated in Patent Document 1 are shown as apparatuses to be compared with the evaluation system 10 according to this embodiment, and SPF measurement results with respect to filters of "BG18," "ND2%," "ND3%," "ND5.2%," and "ND10%" are shown. BG18 is a glass filter manufactured by SCHOTT AG, and is used as an example of other glass filters whose transmittance (% T) is more wavelength-dependent than various ND glass filters.

Furthermore, FIGS. 9 through 13 are graphs illustrating examples of spectral transmittance with a glass filter. FIGS. 9 through 13 correspond to the example results of FIG. 8.

Figure 9:
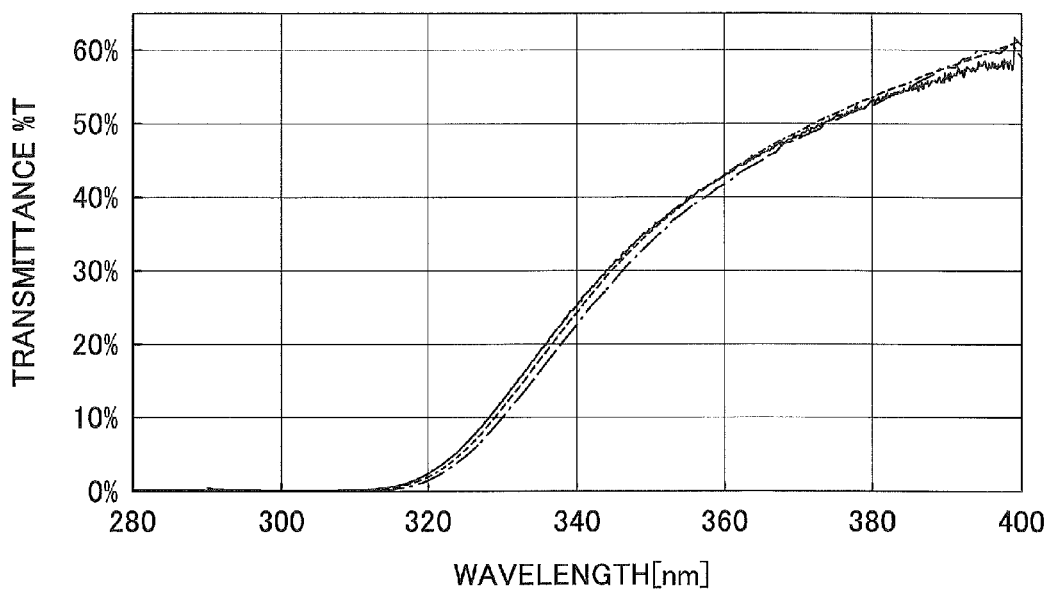
FIG. 9 is a graph illustrating an example of spectral transmittance using a glass filter according to the embodiment illustrated in FIG. 8.
Figure 10:
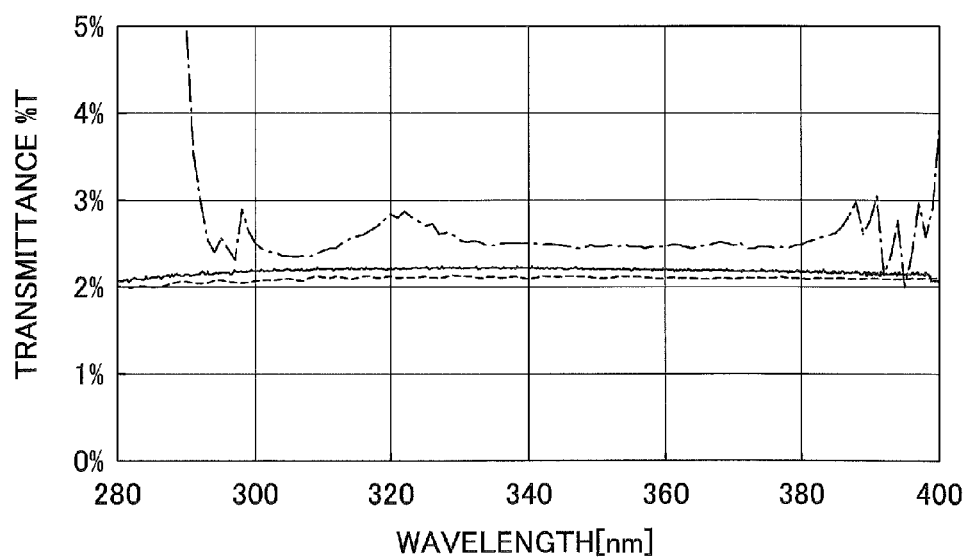
FIG. 10 is a graph illustrating an example of spectral transmittance using a glass filter according to the embodiment illustrated in FIG. 8.
Figure 11:
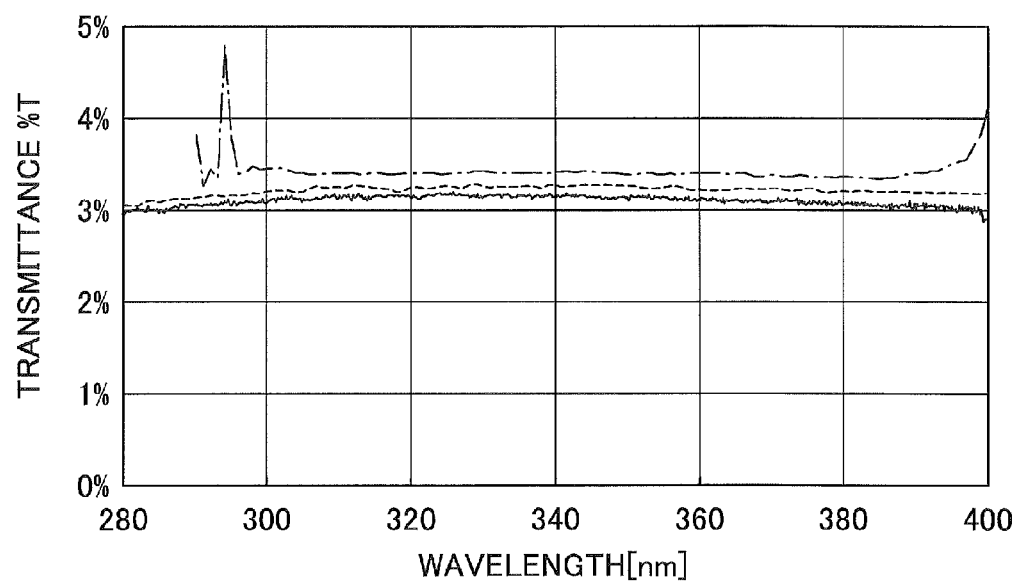
FIG. 11 is a graph illustrating an example of spectral transmittance using a glass filter according to the embodiment illustrated in FIG. 8.
Figure 12:
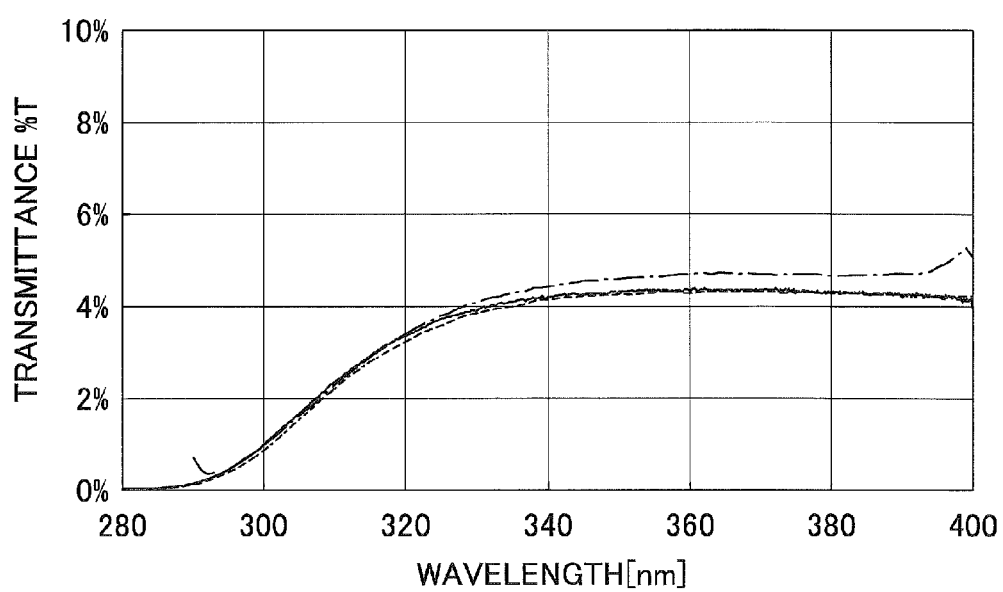
FIG. 12 is a graph illustrating an example of spectral transmittance using a glass filter according to the embodiment illustrated in FIG. 8.
Figure 13:
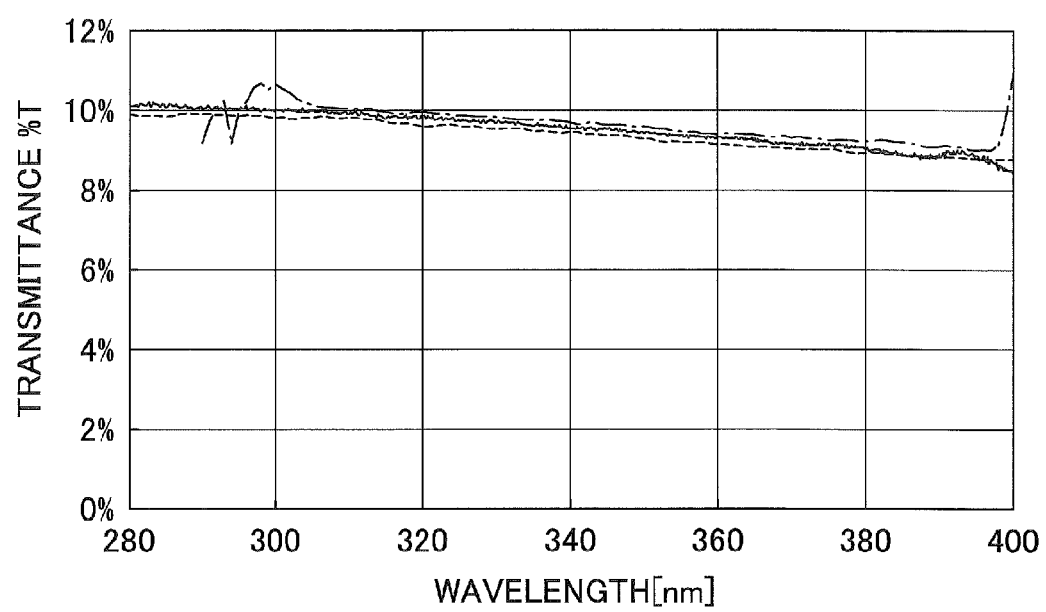
FIG. 13 is a graph illustrating an example of spectral transmittance using a glass filter according to the embodiment illustrated in FIG. 8.

That is, FIG. 9 illustrates spectral transmittance in the case of using the BG18 filter, FIG. 10 illustrates spectral transmittance in the case of using the ND2% filter, FIG. 11 illustrates spectral transmittance in the case of using the ND3% filter, FIG. 12 illustrates spectral transmittance in the case of using the ND5.2% filter, and FIG. 13 illustrates spectral transmittance in the case of using the ND10% filter.

Furthermore, FIGS. 9 through 13 indicate the results of transmittance (% T) with respect to wavelengths of 280 nm to 400 nm in the spectrophotometer, the conventional apparatus, and this embodiment by a broken line, a one-dot chain line, and a solid line, respectively.

Here, as illustrated in the case of FIG. 8, in the case of the BG18 filter, it is possible to measure substantially the same transmittance in the spectrophotometer, the conventional apparatus, and this embodiment. In the case of the ND2%, ND3%, ND5.2% and ND10% glass filters, however, it is found that, in the case of the conventional apparatus, the amount of light is insufficient and the transmittance (erythema transmitted light amount) is not measured with accuracy (unstable) between, for example, approximately 290 nm and 320 nm wavelengths as illustrated in the cases of FIGS. 10 through 13. On the other hand, according to this embodiment, like the spectrophotometer, it is possible to obtain an accurate value with respect to any of the above-described filters.

Figure 14A:
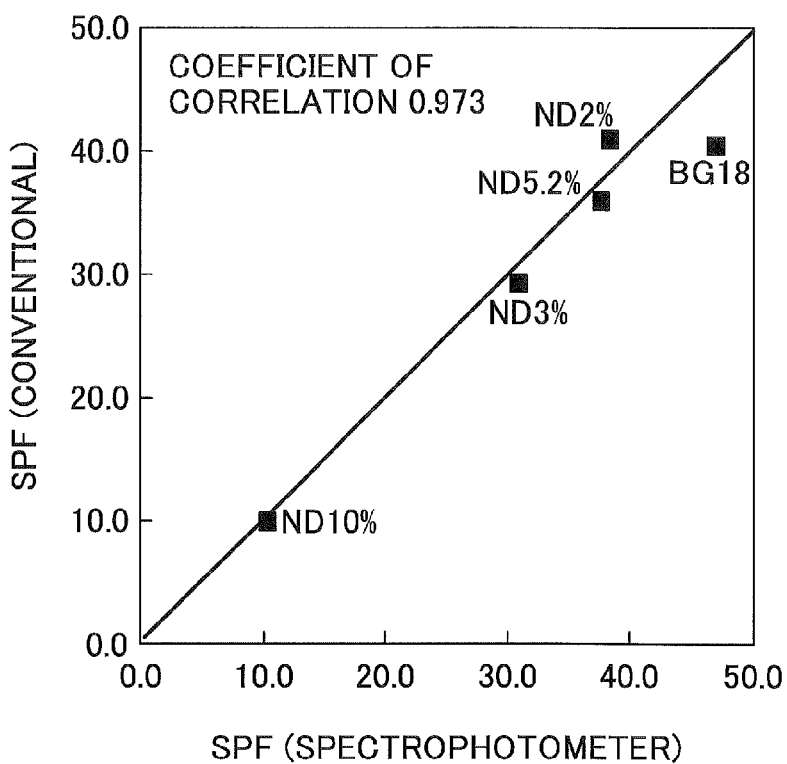
FIGS. 14A and 14B illustrate correlations with a spectrophotometer according to an embodiment of the present invention.
Figure 14B:
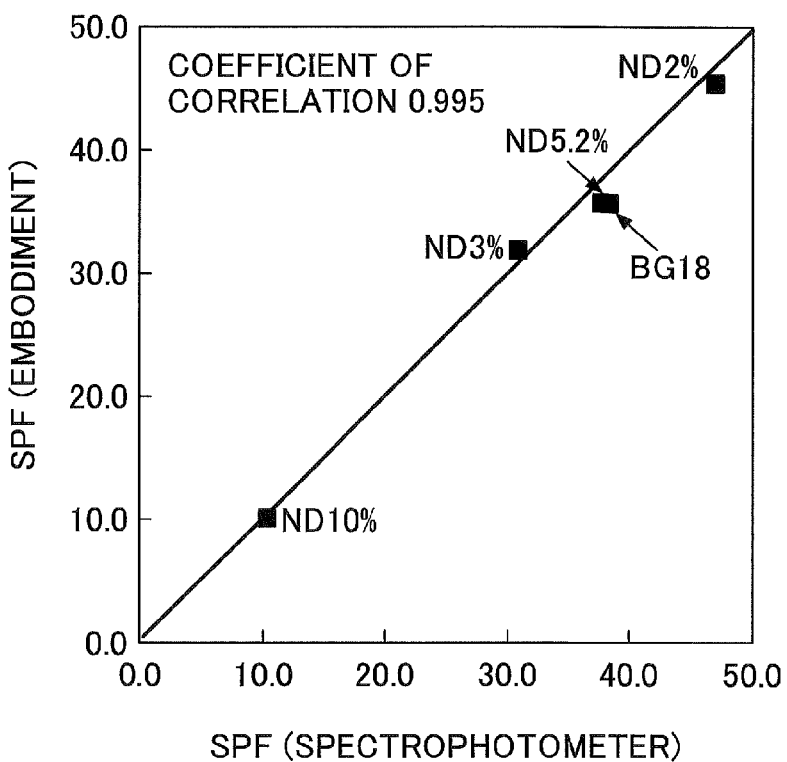

Here, FIGS. 14A and 14B illustrate correlations with the spectrophotometer. FIG. 14A illustrates a correlation between the spectrophotometer and the conventional apparatus, and FIG. 14B illustrates a correlation between the spectrophotometer and this embodiment.

The comparison of the case of FIG. 14A and the case of FIG. 14B shows that the configuration of the evaluation system 10 according to this embodiment is more correlated with the spectrophotometer than the configuration of the conventional apparatus because the coefficient of correlation of FIG. 14B is 0.995 while the coefficient of correlation of FIG. 14A is 0.973. According to this embodiment, it is possible to generate the graphs illustrated in FIGS. 9 through 14B with the above-described screen generation part 48, and it is possible to display and present the generated screens to a user or the like with the output part 42.

As described above, according to an embodiment of the present invention, it is possible to evaluate an ultraviolet radiation protection effect in a short time with high accuracy. Specifically, according to an embodiment of the present invention, by including a part that switches multiple optical filters and measuring spectral radiant intensity by selecting suitable optical filters for ultraviolet irradiation to a sample application part and for measuring the spectral transmittance of the sample application part, it is possible to, for example, improve the measurement accuracy on the short wavelength side. Furthermore, by using an embodiment of the present invention, it is possible to improve the stability of the evaluation result of an ultraviolet radiation protection effect that takes photodeterioration into consideration.

Furthermore, according to an embodiment of the present invention, a spectrometer that uses a linear image sensor and includes no mechanically movable part is used instead of mechanically performing a sequential scan for approximately 2 minutes using a photomultiplier tube and a monochromator as in conventional techniques. As a result, it is possible to obtain the spectral intensity of light transmitted through the sample application part with respect to the entirety of a specified wavelength range at a time in a short time (for example, selectable within the range of 0.01 seconds to 10 seconds in the spectrometer). Accordingly, it is possible to reduce time in which a filter for measuring spectral transmittance is selected.

Furthermore, according to an embodiment of the present invention, it is possible to improve the efficiency of light collection by using a lens and a synthetic quartz light pipe or the like in place of an integrating sphere having poor efficiency of light collection. Furthermore, a photomultiplier in conventional techniques expands the dynamic range by changing the signal amplification factor. On the other hand, in the case of a linear image sensor as illustrated in the embodiments of the present invention, it is possible to expand a final dynamic range by combining, in the evaluation apparatus, multiple results successively obtained by changing not the signal amplification factor but the exposure (integration) time.

A description is given above of a method and apparatus for evaluating an ultraviolet radiation protection effect and a recording medium based on embodiments. All examples and conditional language provided herein, however, are intended for pedagogical purposes of aiding the reader in understanding the invention and the concepts contributed by the inventors to further the art, and are not to be construed as limitations to such specifically recited examples and conditions, nor does the organization of such examples in the specification relate to a showing of the superiority or inferiority of the invention. Although one or more embodiments of the present invention have been described in detail, it should be understood that various changes, substitutions, and alterations could be made hereto without departing from the spirit and scope of the invention.

Elements, expressions, and any combinations of elements of the present invention may be effectively applied to a method, an apparatus, a system, a computer program, a recording medium, a data structure, etc., as embodiments of the present invention.

The present application is based upon and claims the benefit of priority of Japanese Patent Application No. 2012-270006, filed on Dec. 11, 2012, the entire contents of which are incorporated herein by reference.

DESCRIPTION OF THE REFERENCE NUMERALS 10 evaluation system
11 PC (evaluation apparatus)
12 light source
13 filter part
14 filter switching part
15 rod lens
16 light pipe
17 spectrometer
21 housing
22 mirror
23 holder
24 condenser lens
30 application plate
41 input part
42 output part
43 storage part
44 light source control part
45 filter switching control part
46 spectral transmittance measurement part
46a first measurement part 46b second measurement part
47 evaluation part
48 screen generation part
49 transmission and reception part
50 control part
61 input device
62 output device
63 drive unit
64 secondary storage device
65 primary storage device
66 CPU
67 network connection device
68 recording medium
70 screen
71 measurement parameter setting region
72 count status display region
73 transmission spectrum result display region
74 SPF calculation result display region

The invention claimed is:

1. An evaluation method for evaluating an ultraviolet radiation protection effect in a measurement sample applied on an application object member, comprising:
   a first step of switching to a first filter for measuring a spectral transmittance before photodeterioration in a predetermined wavelength range by emission of light including ultraviolet radiation from a light source according to a preset light emission condition, and measuring the spectral transmittance;
   a second step of switching to a second filter for ultraviolet irradiation and causing the photodeterioration of the application object member for a predetermined time by the emission of the light from the light source after the measurement by the first step, and thereafter, switching to the first filter and measuring the spectral transmittance; and
   a third step of evaluating the ultraviolet radiation protection effect based on a change over time in the spectral transmittance obtained by repeating the second step over a predetermined time or a predetermined number of times,
   wherein each of the first filter and the second filter includes a plurality of light source filters corresponding thereto, and the first filter includes ND filters switchable in accordance with an amount of light of the light source in said plurality of light source filters.

2. The evaluation method as claimed in claim 1, wherein the spectral transmittance obtained by the first step and the second step obtains a spectral intensity of light transmitted through the application object member using a linear image sensor.

3. The evaluation method as claimed in claim 1, wherein the light emitted from the light source is caused to be collected using a predetermined lens and a synthetic quartz light pipe.

4. An evaluation apparatus for evaluating an ultraviolet radiation protection effect in a measurement sample applied on an application object member, comprising:
   a light source control part configured to control a light source so as to emit light including ultraviolet radiation according to a preset light emission condition;
   a filter switching part configured to switch a plurality of filters for adjusting a wavelength range of the light source; and
   a spectral transmittance measurement part configured to measure a spectral transmittance of the application object member due to the light source, using the light source control part and the filter switching control part,
   wherein the spectral transmittance measurement part includes
      a first measurement part configured to switch to a first filter for measuring the spectral transmittance before photodeterioration in a predetermined wavelength range by emission of the light from the light source, and to measure the spectral transmittance; and
      a second measurement part configured to switch to a second filter for ultraviolet irradiation and cause the photodeterioration of the application object member for a predetermined time by the emission of the light from the light source after the measurement after the first measurement part, and thereafter, to switch to the first filter and measure the spectral transmittance, and
   wherein each of the first filter and the second filter includes a plurality of light source filters corresponding thereto, and the first filter includes ND filters switchable in accordance with an amount of light of the light source in said plurality of light source filters.

5. The evaluation apparatus as claimed in claim 4, further comprising:
   an evaluation part configured to evaluate the ultraviolet radiation protection effect based on a change over time in the spectral transmittance obtained by repeating the measurement by the second measurement part over a predetermined time or a predetermined number of times.

6. The evaluation apparatus as claimed in claim 4, wherein the spectral transmittance obtained by the first measurement part and the second measurement part obtains a spectral intensity of light transmitted through the application object member using a linear image sensor.

7. The evaluation apparatus as claimed in claim 4, wherein the light emitted from the light source is caused to be collected using a predetermined lens and a synthetic quartz light pipe.

8. A non-transitory computer-readable recording medium with an evaluation program for causing a computer to operate as the evaluation apparatus as claimed in claim 4 being recorded thereon.

* * * * *